United States Patent [19]

Heikkilä et al.

[11] Patent Number: 5,081,026

[45] Date of Patent: Jan. 14, 1992

[54] METHOD FOR THE PRODUCTION OF XYLITOL

[75] Inventors: Heikki Heikkilä; Juha Nurmi; Leena Rahkila, all of Espoo; Marja Töyrylä, Kirkkonummi, all of Finland

[73] Assignee: Suomen Xyrofin Oy, Kotka, Finland

[21] Appl. No.: 611,383

[22] Filed: Nov. 2, 1990

Related U.S. Application Data

[63] Continuation of Ser. No. 297,791, Jan. 17, 1989, abandoned.

[51] Int. Cl.$^5$ .......................... C12P 7/18; C12P 7/08; C12R 1/645; C12R 1/74

[52] U.S. Cl. .......................... 435/158; 435/163; 435/800; 435/803; 435/911; 435/924

[58] Field of Search ............... 435/158, 800, 803, 911, 435/924, 163

[56] References Cited

U.S. PATENT DOCUMENTS

| | | | |
|---|---|---|---|
| 3,619,369 | 11/1971 | Onishi et al. | 435/158 |
| 4,096,036 | 6/1978 | Liu et al. | 435/94 |
| 4,368,268 | 1/1983 | Gong | 435/161 |

FOREIGN PATENT DOCUMENTS

| | | | |
|---|---|---|---|
| 0024834 | 8/1970 | Japan | 435/158 |
| 0145095 | 7/1985 | Japan | 435/158 |
| 1063291 | 4/1986 | Japan | 435/158 |
| 2104588 | 5/1987 | Japan | 435/158 |

OTHER PUBLICATIONS

Ditzelmüller, Kubicek, Wöhrer and Röhn, Xylitol Dehydrogenase from Pachysolen Tannophilus, Microbiology Lett. 25, pp. 195–198, 1984.

*Primary Examiner*—Herbert J. Lilling
*Attorney, Agent, or Firm*—Baker & McKenzie

[57] ABSTRACT

A method is disclosed for the production of xylitol from a xylose and/or xylan containing material. A solution containing xylitol and other hexoses is fermented with a yeast strain capable of converting free xylose to xylitol and other free hexoses present to ethanol, with the xylitol subsequently separated by chromatographic separation means.

28 Claims, 4 Drawing Sheets

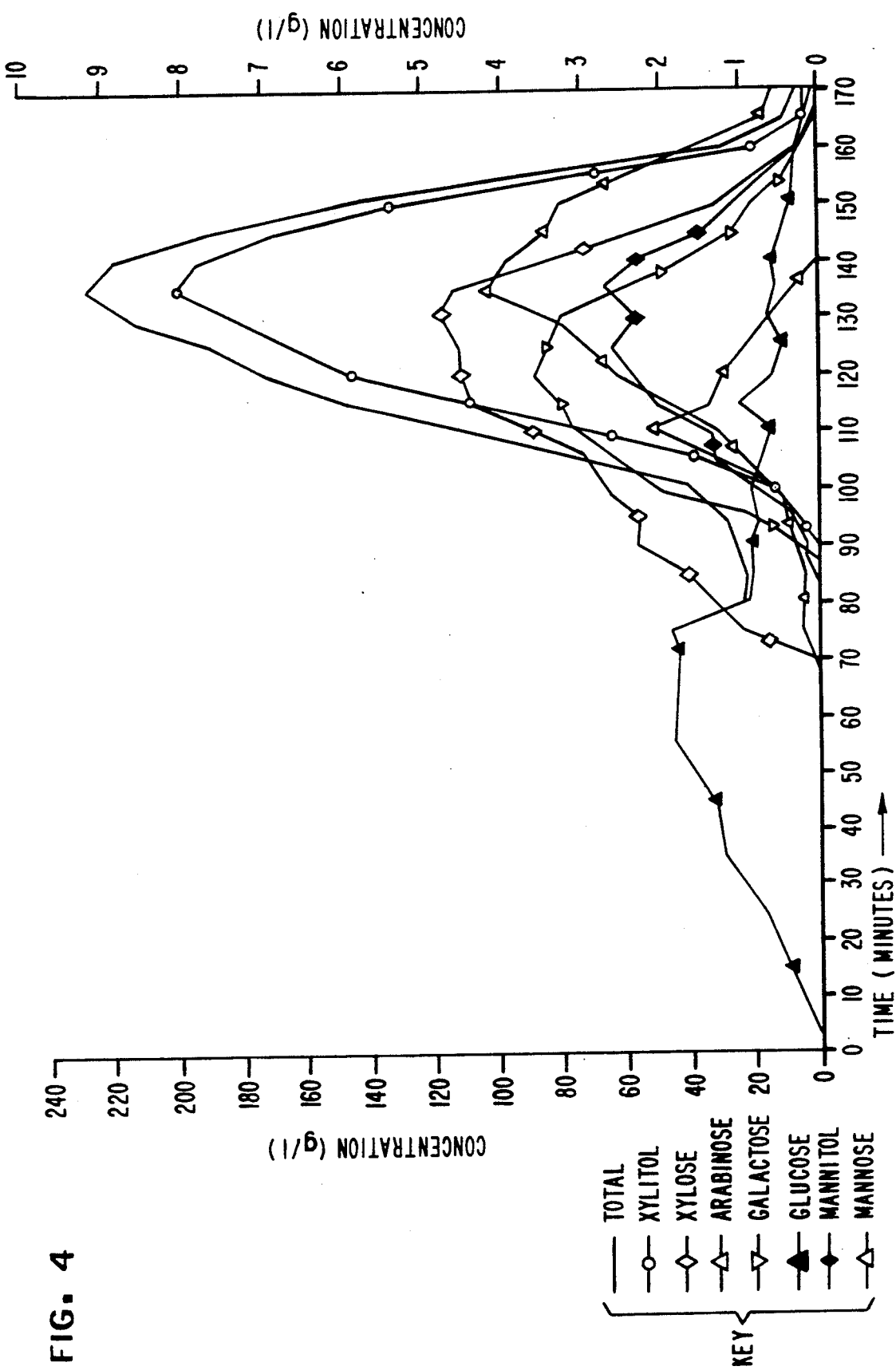

5,081,026

METHOD FOR THE PRODUCTION OF XYLITOL

This application is a continuation of application Ser. No. 297,791, filed Jan. 17, 1989, now abandoned.

TECHNICAL FIELD

This invention relates to a method for the production of xylitol from a xylose and/or xylan-containing material, and in particular, from biomass hemicellulose hydrolysates. A specific aspect of this invention relates to a method for the production of xylitol by fermentation of biomass hemicellulose hydrolysates with a yeast strain capable of converting free xylose to xylitol and enrichment of the xylitol concentrations by chromatographic separation for crystallization.

BACKGROUND OF THE INVENTION

The pentahydric alcohol xylitol is the sugar alcohol derived from the reduction of xylose ($C_5H_{10}O_5$). Xylitol is a naturally occurring, five-carbon sugar alcohol which has the same sweetness and caloric content of sugar (4 kilocalories per gram). Xylitol is found in small amounts in many fruits and vegetables and is produced in the human body during normal metabolism. Xylitol has certain known metabolic, dental and technical characteristics which make it an attractive sugar substitute in various contexts Xylitol is metabolized independently of insulin, so it can be safely consumed by non-insulin dependent diabetics Further, xylitol has been shown to delay gastric emptying and to possibly suppress food intake which means it may have an important role in weight reducing diets.

Xylitol is also a non-cariogenic, and possibly even a cariostatic substance. In the mouth, sucrose and other carbohydrates are fermented by *Streptococcus mutans* and other bacteria, generating acid which lowers the pH, demineralizes tooth enamel and leads to dental caries. *S. mutans* and other acid by-products of fermentation which contribute to tooth decay. Studies have also produced data which suggests that xylitol may even actively suppress the formation of new caries and may even "reverse" existing lesions by inducing remineralization.

From a taste perspective, xylitol does not typically manifest an unpleasant aftertaste like other sugar substitutes and, because of the high energy required to dissolve one gram of xylitol, it produces a pleasant "cooling" effect in the mouth.

Despite xylitol's advantages, the utilization of xylitol on a commercial scale has been limited by its relatively high cost, due to the difficulty of its production on a commercial scale. Xylitol is generally prepared from xylan-containing material, particularly hydrolysates of hemicelluloses. Hemicelluloses are a large group of well characterized polysaccharides found in the primary and secondary cell walls of all land and freshwater plants. Hemicelluloses are made up of sugar residues, among others D-xylose and including D-mannose, D-glucose, D-galactose and L-arabinose.

In prior art methods, xylitol has been prepared from xylan-containing material by hydrolyzing the material to produce a mixture of monosaccharides, including xylose. The xylose is converted to xylitol, generally in the presence of a nickel catalyst such as Raney-nickel. The prior art reveals a number of methods for the production of xylose and/or xylitol from xylan-containing material. Included in such prior art methods are U.S. Pat. No. 3,784,408 (Jaffe et al.), U.S. Pat. No. 4,066,711 (Melaja et al.), U.S. Pat. No. 4,075,405 (Melaja et al.), U.S. Pat. No. 4,008,285 (Melaja et al.) and U.S. Pat. No. 3,586,537 (Steiner et al.).

These prior art methods are, however, complicated multi-step processes which are relatively expensive and inefficient. The prior art recognizes that one of the principal problems in this context is the efficient and complete separation of xylose and/or xylitol from polyols and other by-products of hydrolysis in order to obtain xylitol of sufficient purity. In order to address this fundamental concern, multistep separation techniques, including mechanical filtration and chromatographic separation are generally required. In addition, the art teaches the use of other purification methods, such as the use of acids to precipitate lignins which generally increase the time and expense of xylitol production on a commercial scale.

It is known that certain yeasts possess the enzyme xylose reductase which catalyzes the reduction of D-xylose to xylitol as the first step in D-xylose metabolism. Studies, on an experimental scale, have utilized yeast cells capable of fermenting D-xylose or cell-free extracts containing xylose reductase to produce xylitol from D-xylose rich starting material. Gong, et al., Quantitative Production of Xylitol From D-Xylose By a High Xylitol Producing Yeast Mutant Candida Tropicalis HXP2, Biotechnology Letters, Vol. 3, No. 3, 125–130 (1981); Kitpreechavanich, V. et al.: Conversion of D-Xylose Into Xylitol By Xylose Reductase From Candida Pelliculosa Coupled With the Oxidoreductase System of Methanogen Strain HU, Biotechnology Letters, Vol. 10, 651–656 (1984); McCracken and Gong, Fermentation of Cellulose and Hemicellulose Carbohydrates by Thermotolerant Yeasts, Biotechnology and Bioengineering Symp. No. 12, pp. 91–102 (John Wiley & Sons 1982). Although yeast strains exist which are capable of producing high yields of xylitol from the fermentation of D-xylose, a complete process for producing xylitol from, for example, biomass hemicellulose hydrolysates which contain xylose in addition to hexoses and other impurities on a commercial scale has not been disclosed by the prior art.

The present invention, however, discloses an efficient method of producing relatively high purity xylitol from xylose-containing starting material which utilizes yeast strains capable of converting xylose to xylitol and most hexoses present to ethanol; such fermentation produces a xylitol rich solution from which xylitol can be simply and efficiently recovered without resort to any extensive and expensive separation expedients. Generally, the xylitol can be purified in one step by chromatographic separation and subsequently crystallized. Small amounts of ethanol are easily removed by evaporation or similar expedients, thereby avoiding the need for extensive techniques to separate the xylitol from hexitols and other sugars generated by hydrolysis and conventional hydrogenation and which are present in the xylitol rich solution.

SUMMARY OF THE INVENTION

The present invention contemplates a method for the production of substantially pure xylitol from an aqueous xylose solution which may also contain hexoses such as glucose as well as other impurities. The invention contemplates fermenting said solution using a yeast strain capable of converting substantially all of said free xylose to xylitol and most of said free hexoses to ethanol. The fermented product is purified by removing yeast cells from the solution by filtration, centrifugation or other suitable expedients and removing ethanol by evaporation or distillation. Chromatographic separation yields a xylitol rich fraction or fractions from which xylitol can be crystallized.

In some cases, pretreatment of the aqueous xylose solution is utilized. Such pretreatment may include posthydrolysis and/or separation steps in order to remove components which may be toxic and/or harmful to the yeast used to convert the xylose to xylitol or other impurities which may adversely affect the subsequent fermentation and separation steps. Such pretreatment steps can include chromatographic separation techniques. The present invention utilizes yeasts capable of reducing xylose to xylitol and hexoses to ethanol. Such yeasts include, but are not limited to, yeasts of the genus candida, pichia, pachysolen and debaryomyces. Of these genera, Candida and Debaryomyces are preferred with *Candida tropicalis* and *Debaryomyces hansenii* being particularly preferred. One good example is the Candida tropicalis strain deposited in the American Type Culture Collection and assigned Accession Number 9968.

BRIEF DESCRIPTION OF THE DRAWINGS

FIG. 1 sets forth an elution profile for the chromatographic separation of a xylose-rich fraction after fermentation with *Debaryomyces hansenii* yeast cells.

FIG. 2 sets forth an elution profile for the chromatographic separation of a steam exploded, post-hydrolyzate showing the concentration of xylitol, arabinose, rhamnose, mannose, galactose and glucose over time.

FIG. 3 is a fermentation profile of xylose-rich fractions fermented with *Candida tropicalis* yeast cells showing the concentrations of yeast, xylose, xylitol and ethanol over time.

FIG. 4: FIG. 4 is an elution profile for the chromatographic separation of a xylose-rich fraction after fermentation with *Candida tropicalis* yeast cells showing the concentrations of xylitol, xylose, arabinose, mannose, galactose, glucose, and mannitol over time.

DETAILED DESCRIPTION OF THE PREFERRED EMBODIMENT

A. General

1. Starting Materials

Figure 1:
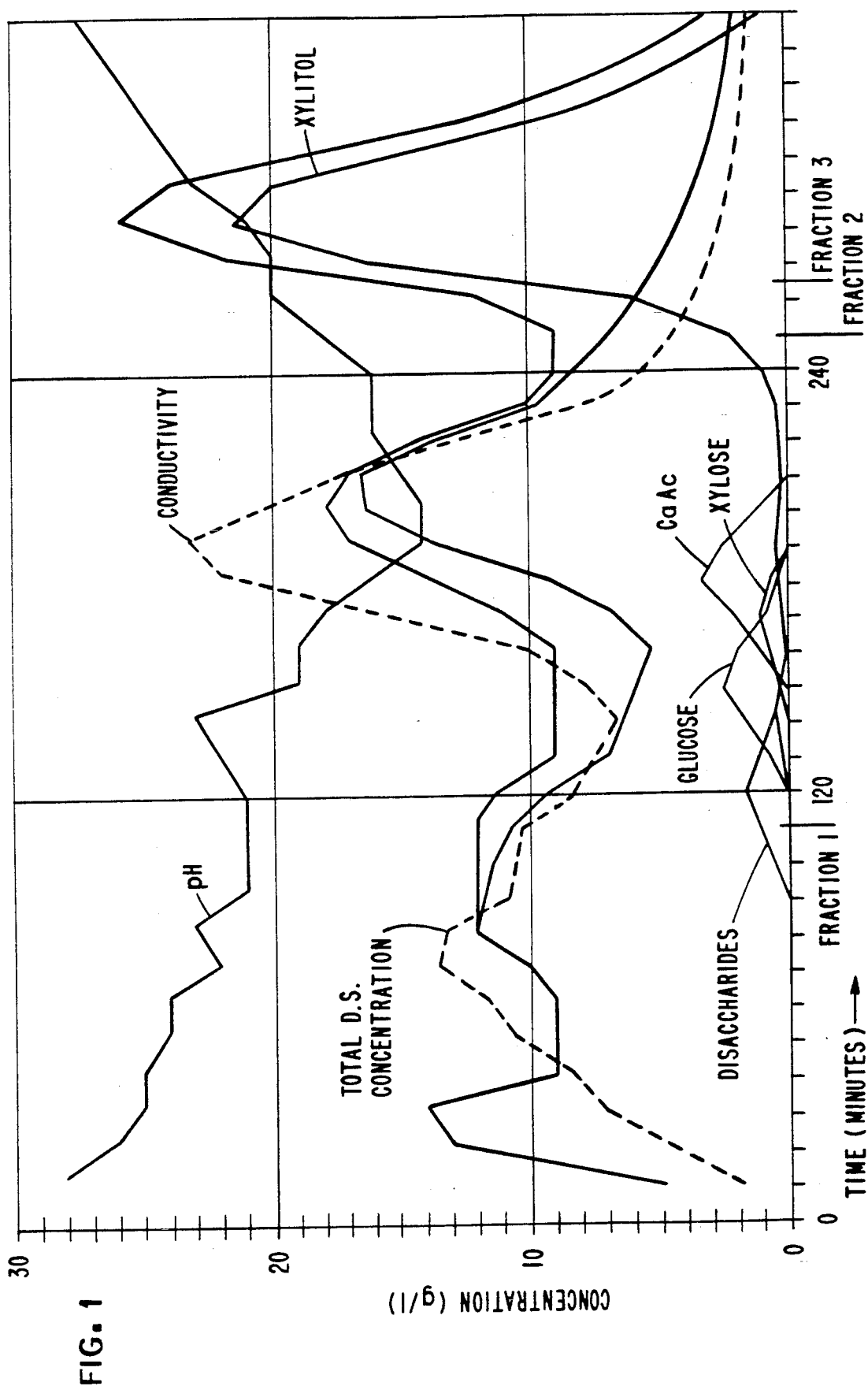
FIG. 1.

The starting materials for use with the methods of the present invention include almost any xylan-containing material. Potential starting materials include deciduous trees (such as birch, beech, poplar, alder and the like) and such plants or plant components as corn or maize, oat hulls, corn cobs and stalks, nut shells, straws, bagasse and cotton seed hulls. When wood is utilized as the starting material, it is preferably ground into chips, sawdust, shavings and the like and subjected to hydrolysis, or steam explosion and hydrolysis which creates hemicellulose material which can be used with the instant invention.

In addition to the above-listed materials, xylan or xylose-rich byproducts from wood processing procedures are also effective raw materials. For example, the spent liquor produced as a waste product from the production of wood pulp via the sulfite process — known as "sulphite-spent liquors" - contains undissolved wood solids, lignins, hexoses and pentoses, including xylose, and is an effective starting material for the production of xylitol. Other byproducts or waste products from paper or pulp processing which are xylan or xylose-rich can also be used.

In order to utilize the methods of the instant invention, an aqueous solution containing free xylose is required. Therefore, the hydrolysis of the starting material by acids or enzymes to break down xylan to xylose may be required. For example, U.S. Pat. Nos. 3,784,408 (Jaffe et al) and U.S. Pat. No. 3,586,537 (Steiner et al) disclose methods for hydrolyzing xylan-containing material to produce xylose-rich solutions.

2. Fermentation of xylose-containing aqueous solutions

The starting material may be treated before fermentation, if necessary, to remove any constituents which might be toxic or otherwise harm the yeast for fermentation Whether such pretreatment is necessary depends o the starting material involved and the yeast which will be utilized for fermentation. Suitable pretreatment of raw material may include post-hydrolysis and/or separation steps. The concentration of xylose in the aqueous solution suitable for fermentation depends on the starting material utilized, but preferably is in the range of about 50 g/L to about 300 g/L.

To effect fermentation, the present invention utilizes a yeast strain which has the ability to convert xylose to xylitol, and most hexoses present to ethanol. Ethanol can be easily recovered by evaporation, distillation, or other known candida, pichia, pachysolen and debaryomyces, expedients much more simply and more efficiently than separation of xylose and/or xylitol from other sugars.

An example of a yeast strain which is suitable in this context is a *Candida tropicalis* deposited with the American Type Culture Collection (No. 9968). Other yeast strains include those of the genera Candida, Pichia, Pachysolen and Debaryomyces, (See N.J.W. Kregr-van Rij, The Yeast. A Taxonomic Study, 3 ed., Elsevier Science Publishers B.V. 1984.) which are capable of converting xylose to xylitol and hexoses to ethanol.

Prior to fermentation of the xylose-rich solution, the solution can be subjected to chromatographic separation to separate and remove larger molecules and ionized substances, when low purity liquids are used as raw material. For example, pre-fermentation chromatographic separation may be advantageous when sulfite spent liquors are used for the starting material.

Fermentation of the xylose-rich solution can take place in most commercially available batch fermenters equipped with aeration, agitation and pH control is preferred; for example, a Braun-Biostat [Model #E] at a temperature of about 10° C. to about 45° C. The preferred temperature for fermentation is in the range of about 25° C. to about 35° C., with a temperature of about 30° C. being particularly preferred. Yeast cells are added to the xylose-rich solution; generally, the higher the concentration of yeast, the faster the fermentation will proceed. The optimum concentrations of yeast depends on the xylose liquor and its characteristics and xylose concentration in the liquor. We have found that adding yeast cells to a concentration of between about 0.1 g and about 10 g dry yeast/L (dry weight) substrate is preferred when the xylose concentration is between about 50 g/L and about 300 g/L.

Fermentation is enhanced by the addition of nutrients, and continues until most of the xylose has been converted to xylitol, and substantially all of the hexoses have been converted to ethanol; typically, fermentation will take between about 24 and about 144 hours, with a fermentation time of about 24–72 hours being particularly preferred. Using the method of the present invention, it is possible to convert over 90% of the xylose to xylitol.

3. Post-fermentation purification and xylitol separation

Following fermentation, the solution is clarified prior to separation of xylitol. In a batch fermentation process, the yeast cells are removed following the completion of fermentation. The removal of yeast cells can be accomplished by centrifugation, filtration or similar expedients. Once the yeast cells have been removed and the solution is clear, the ethanol produced by fermentation can be removed by evaporation, distillation or other expedients at this stage.

After removal of the yeast cells (and possibly ethanol), the xylitol in the fermented solution is enriched by means of chromatographic separation. Such chromatographic separation is preferably carried out in a column packed with sulfonated polystyrene resin cross-linked with divinyl benzenes in an alkali/alkaline earth metal form. A method for large scale chromatography suitable for use in this context is described in U.S. Pat. No. 3,928,193 (Melaja et al.). Chromatographic separation can also take place as a continuous process, utilizing a simulated moving bed process, as disclosed in U.S. Pat. No. 2,985,589, also utilizing a DVB cross-linked sulfonated polystyrene resin.

Xylitol from xylitol-rich fractions derived from chromatographic separation can subsequently be crystallized in high yield utilizing conventional crystallization techniques including cooling and boiling crystallization. If cooling crystallization is used, the xylitol-rich fraction is seeded with xylitol crystals having an average diameter of about 30 microns, and the temperature of the solution is gradually lowered. The resulting crystals, preferably with an average diameter of about 250 to about 600 microns, are separated by centrifugation and washed with water to recover substantially pure crystalline xylitol.

B. Experimental

EXAMPLE I

Production of Xylitol from "Sulfite-Spent Liquor"

Xylitol was produced from a "sulfite-spent liquor" from hardwood utilizing fermentation with a *Debaryomyces hansenii* yeast established as a strain which could ferment xylose to xylitol and most hexoses to ethanol. A batch of sulfite spent liquor (from the production of birchwood pulp) was treated as described in U.S. Pat. No. 4,631,129 to obtain a xylose-rich fraction. The analysis of this fraction was as follows (carbohydrate composition measured by gas liquid chromatography analysis):

| | |
|---|---|
| Dry substance | 30.4 w/w |
| pH | 2.5 |
| Calcium (CA ++) | 2.0% on dry substance (hereinafter "d.s.") |
| Sodium (Na +) | 0.1% on d.s. |
| Carbohydrates: | |
| Xylose | 39.3% on d.s. |

| -continued | |
|---|---|
| Arabinose | 1.0% on d.s. |
| Rhamnose | 1.2% on d.s. |
| Glucose | 2.5% on d.s. |
| Mannose | 0.1% on d.s. |
| Galactose | 2.0% on d.s. |

The fraction was neutralized with calcium oxide to a pH of about 6.2 by adding 10 g CaO per liter of the fraction. The fraction was then diluted to a concentration of 51 g xylose per liter of solution and then fermented with yeast cells. The fermentation was carried out in "shake" flasks (200 ml) at about 25° C. for about 48 hours. The amount of yeast cells added was about $1.7 \times 10^8$ cells per millimeter of fraction which were adapted to the fermentation solution after initial growth in xylose-rich solution. The yeast cells were removed after fermentation for about 48 hours by centrifugation and the resulting clear solution was subjected to chromatographic separation to separate xylitol produced by the fermentation under the following conditions:

| Composition of solution: | |
|---|---|
| Dry substance | 24.0 w/w |
| pH | 5.9 |
| Carbohydrates: | |
| Xylitol | 24.7% on d.s. |
| Xylose | 0.3% on d.s. |
| Glucose | 2.1% on d.s. |
| Arabinose | 0.6% on d.s. |
| Calcium acetate | 2.5% on d.s. |
| Column: | |
| Diameter | 10 cm |
| Height | 200 cm |
| Resin | Zerolit 225 polystyrene-dvb-cation exchanger in calcium form, mean particle size 0.32 mm, divinylbenezene ("DVB") content 3.5% |
| Flow rate | 50 ml/min |
| Temperature | 65° C. |
| Feed volume | 500 ml |

The elution profile from the column is shown in FIG. 1. Samples were taken from the outflow and analyzed for dry substance and composition as set forth below in Table I with the outflow divided into three fractions:

TABLE I

| Sample Analysis | | | |
|---|---|---|---|
| | Fraction #1 | Fraction #2 | Fraction #3 |
| Dry substance (grams) | 134 | 10 | 58 |
| Concentration (g/l) | 12 | 10 | 16 |
| Xylitol (% on d.s.) | 0.7 | 40.0 | 79.0 |

Crystallization of xylitol produced by the fermentation method described above was accomplished as follows. A xylitol-rich fraction was prepared as described above. The composition of a xylitol fraction utilized was:

| | |
|---|---|
| Dry substance | 20 g per liter |
| Xylitol | 86.6% on d.s. |
| Others | 13.4% on d.s. |

From this solution xylitol was recovered by cooling crystallization The solution was first evaporated to 86.5% dry substance concentration and transferred to a crystallizer equipped with cooling system and agitator.

The initial temperature was about 65° C. and the pH was about 5.3. The solution was seeded with xylitol crystals suspended in isopropanol with a crystal diameter of about 30 microns. The temperature was lowered during 3 hours from about 65° C. to about 50° C. Under these conditions, the xylitol crystals grew to an average diameter of 250 micron. The crystals were separated from the solution by centrifugation and washed with water. The recovered crystals consisted of over 99% pure xylitol.

EXAMPLE 2

Production of Xylitol from Steam Exploded Birchwood

The raw material for this example was a steam-exploded birch wood hydrolyzate subjected to posthydrolysis in order to break down the xylan to free xylose. For parameters of the hydrolysis utilized in this example hydrolysis, refer to "Enzymatic hydrolysis of steam-pretreated lignocellulosic material," Poutanen, K. and Puls, J., Proc. 3rd Eur. Congr. Biotechnol., Munich 1984, Vol. II, pp. 217-222. The composition of the resulting xylose-rich solution was following:

| Components | Concentration (g/l) |
|---|---|
| Xylose | 76 |
| Glucose | 3.6 |
| Rhamnose | 1.3 |
| Mannose | 2.1 |
| Galactose | 2.4 |
| Arabinose | 0.8 |

Total dry material was 15% by weight of the solution

The solution was fermented with *Candida tropicalis* yeast (ATCC 9968). The pH of the solution was adjusted to about 6 by the addition of 25% NaOH, and inoculated with 3 g/L yeast extract; 3 g/L malt extract and 5 g/L peptone were added as nutrients. The inoculum was prepared by growing the yeast in a 5% xylose solution with the same nutrient addition. During the fermentation the temperature was about 30° C. The fermentation was carried out in a Braun Biostat fermenter [Model #E] supplied with aeration (0.18 L/min) and agitation (200 rpm) and pH-control (25% NaOH) to maintain a pH of 6; the fermenter had a working volume of 8 L and a total volume 10 L. Foaming was controlled with Mazu 6000 antifoam agent. The analysis of samples from the fermentor is shown in Table II. Composition of samples from fermentation was analyzed by high performance liquid chromatography.

TABLE II

| Time/hours | Sample Analysis | | | |
|---|---|---|---|---|
| | Yeast g/l | Xylose g/L | Xylitol g/L | Ethanol g/l |
| 0 | 1.2 | 75.8 | 0.0 | 0.0 |
| 24 | 1.4 | 66.5 | 4.8 | 3.7 |
| 48 | 2.0 | 55.2 | 14.1 | 6.9 |
| 72 | 2.6 | 37.3 | 29.4 | 7.7 |
| 96 | 2.8 | 18.7 | 54.2 | 7.6 |
| 120 | (not measured) | 9.4 | 61.9 | 8.5 |
| 144 | (not measured) | 3.0 | 52.7 | 6.7 |

Xylitol contained in the solution obtained by fermentation was concentrated in xylitol-rich fractions by chromatographic separation and crystallized to obtain 99% pure xylitol as in Example 1.

EXAMPLE 3

Production of Xylitol from Steam Exploded Birchwood

In Example 3, the raw material utilized was a steam exploded, posthydrolysate from birch wood according to the parameters discussed in Example 2. The composition of the solution was:

| Component | Concentration (g/l) |
|---|---|
| Xylose | 110.0 |
| Glucose | 3.1 |
| Rhamnose | 3.5 |
| Mannose | 3.4 |
| Galactose | 1.5 |
| Arabinose | 1.6 |

Total d.s. concentration was 15% by weight

Prior to fermentation the solution was subjected to a chromatographic separation process to remove most of large molecules and ionized substances. The chromatographic separation was carried out in column filled with AMBERLITE BH-1 (polystyrene-divinylbenzene) resin in sodium form. The conditions were as follows:

Resin: AMBERLITE BH-1 sulphonated polystyrene-divinylbenzene
  cross-linked with 5.5% dvb in sodium form.
Particle size 0.40 mm.
Column diameter 0.225 m and height 5.0 m.
Temperature: 65° C.
Flow Rate: 0.04 m3/h
Feed: 18 L of a solution concentrated to 31.2 weight %.

Figure 2:
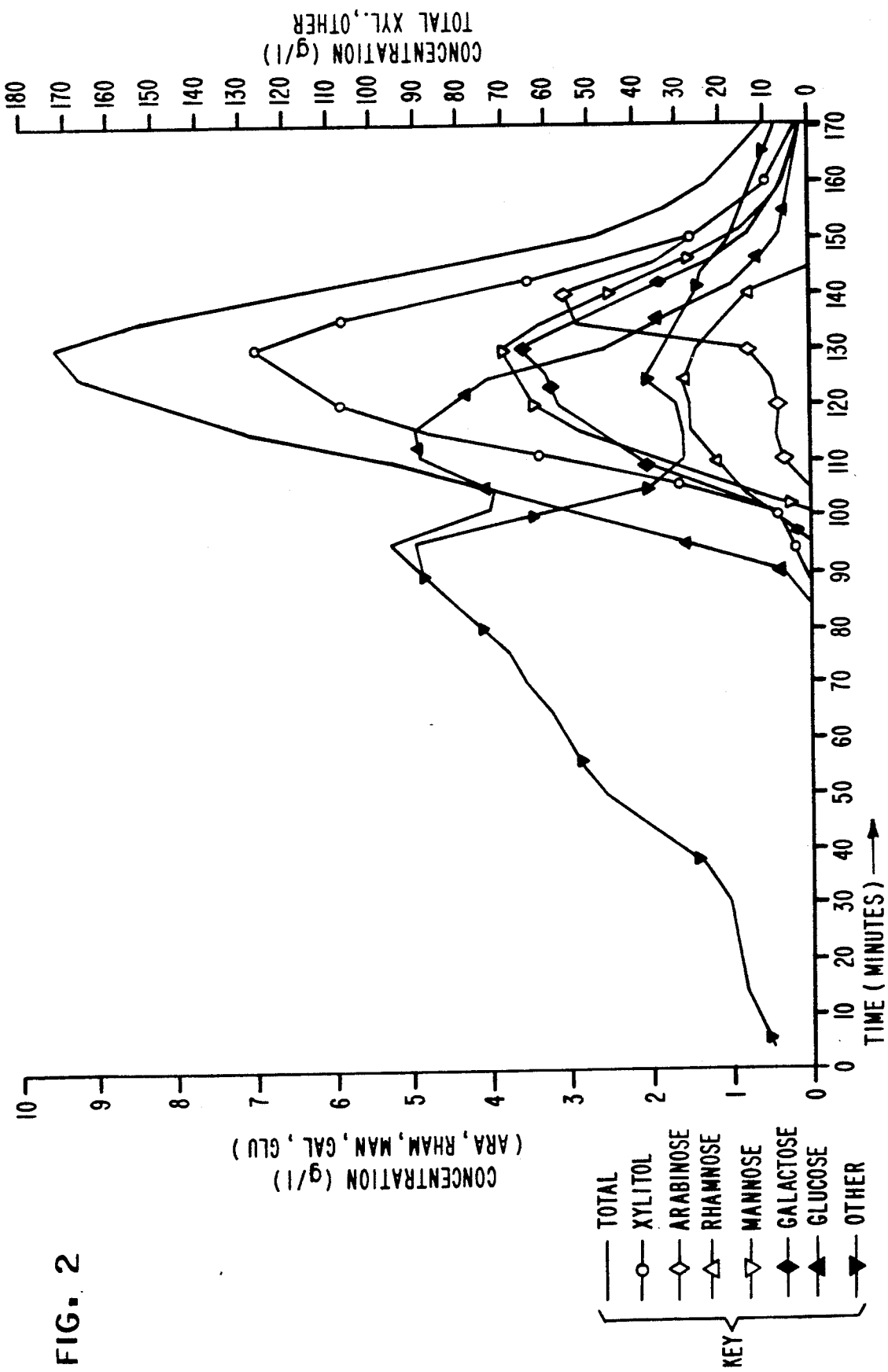
FIG. 2.

The result of the chromatographic separation described above is shown graphically in FIG. 2. Samples were taken at 5 minute intervals. The total cycle time was 170 minutes.

Composition of the feed solution into the separation column was as follows:

| Arabinose | 0.6% on d.s. |
|---|---|
| Rhamnose | 0.5% on d.s. |
| Xylose | 37.8% on d.s. |
| Mannose | 1.2% on d.s. |
| Galactose | 1.6% on d.s. |
| Glucose | 1.6% on d.s. |
| Others | 57.3% on d.s. |

The eluent was divided in 5 fractions. Fraction 2 was discarded from the process and Fraction 4 was collected for the fermentation step. The remaining fractions were returned to the feed solution for the chromatographic separation to increase separation yield. The composition of the fractions is shown below in Table III.

TABLE III

| | Analysis of Fractions | | | | |
|---|---|---|---|---|---|
| | Fraction | | | | |
| | 1 | 2 | 3 | 4 | 5 |
| | Time (minutes) (cut point) | | | | |
| | 15 | 100 | 115 | 140 | 155 |
| Arabinose | 1.3 | 0.1 | 0.2 | 1.0 | 2.1 |
| Rhamnose | 0.0 | 0.0 | 1.2 | 0.9 | 0.0 |
| Xylose | 24.8 | 3.4 | 57.6 | 71.2 | 46.6 |
| Mannose | 0.8 | 0.1 | 1.9 | 2.2 | 1.6 |
| Galactose | 0.8 | 0.1 | 2.0 | 2.0 | 1.4 |
| Glucose | 0.5 | 0.5 | 4.7 | 1.9 | 0.7 |

TABLE III-continued

Analysis of Fractions

| | Fraction | | | | |
|---|---|---|---|---|---|
| | 1 | 2 | 3 | 4 | 5 |
| Time (minutes) (cut point) | | | | | |
| | 15 | 100 | 115 | 140 | 155 |
| Other | 71.9 | 95.8 | 32.3 | 20.3 | 47.6 |

(yield values set forth above are expressed in terms of % on d.s.)

Figure 3:
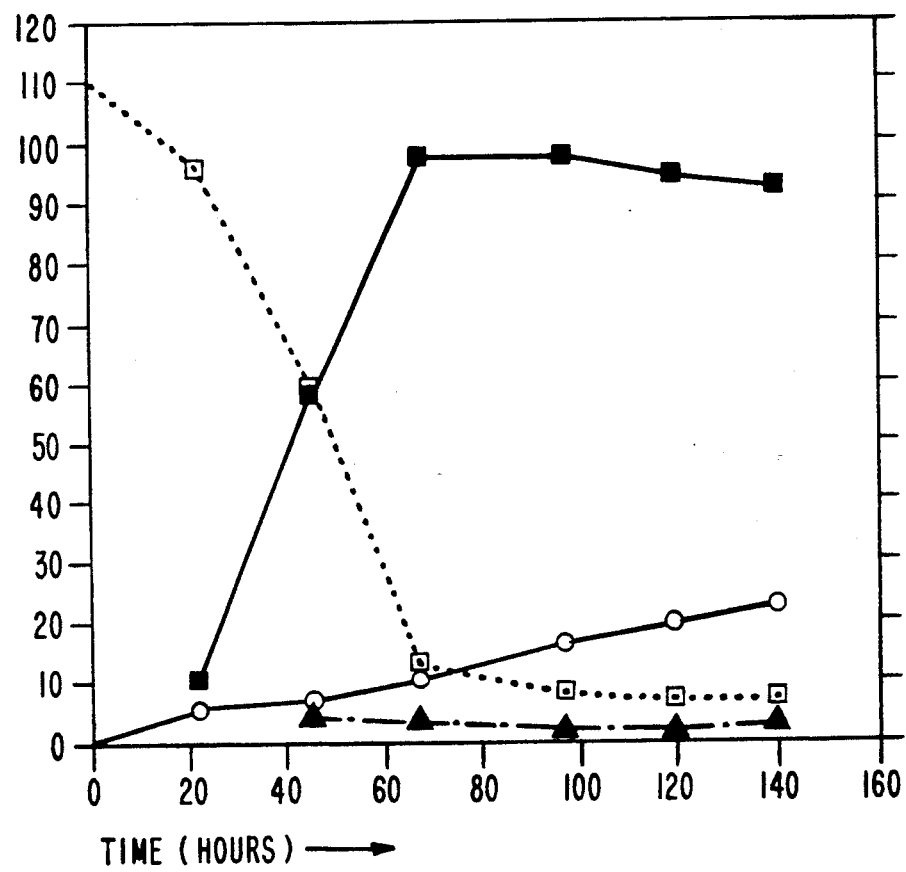
FIG. 3.

The fermentation was carried out with *Candida tropicalis* yeast cells as in Example 2. The results of the fermentation is shown graphically in FIG. 3. The obtained yield of xylitol was over 90 g/L from 100 g/L xylose. The nutrient used in this experiment was (Gistex) yeast extract 15 g/L. The inoculum was grown in a hydrolyzate diluted with water (1/10) with 3% added glucose and 3% added yeast extract.

From the xylitol-rich solution the xylitol was recovered by chromatographic separation using a pilot scale column with the following characteristics:

Column: Height 4.5 m, diameter 0.225 m
Resin: Sulphonated polystyrene polymer cross-linked with 5.5% divinylbenzene. Mean particle size 0.37 mm in Sodium form
Flow rate: 0.03 m3/h
Temperature: 65° C.
Feed Solution: 24 g kg of a 24 weight % solution (dry substance 5.76 kg).

| Composition: | |
|---|---|
| Xylitol | 64.0% on d.s. |
| Xylose | 2.0% on d.s. |
| Arabinose + Mannose | 1.4% on d.s. |
| Galactose + Rhamnose | 1.2% on d.s. |
| Glucose | 0.4% on d.s. |
| Mannitol | 0.9% on d.s. |
| Other | 30.1% on d.s. |

The separation is presented graphically in FIG. 4. Five fractions were recovered. The compositions are shown below in Table IV. Fraction No. 4 was the product fraction from which substantially xylitol was crystallized as set forth in Example 1.

TABLE IV

Composition of Fractions

| | Fraction | | | | |
|---|---|---|---|---|---|
| | 1 | 2 | 3 | 4 | 5 |
| Time minutes (cut point) | | | | | |
| | 10 | 100 | 105 | 155 | 165 |
| Xylitol | 8.7 | 4.9 | 56.3 | 85.0 | 55.6 |
| Xylose | 0.2 | 2.0 | 4.4 | 2.0 | 0.4 |
| Arabinose + Mannose | 3.6 | 0.5 | 1.4 | 1.7 | 4.2 |
| Galactose + Rhamnose | 0.3 | 0.6 | 3.8 | 1.4 | 0.5 |
| Glucose | 0.0 | 0.1 | 1.9 | 0.4 | 0.0 |
| Mannitol | 0.2 | 0.2 | 2.0 | 1.1 | 0.7 |
| Other | 87.1 | 81.8 | 30.2 | 8.5 | 38.5 |

(yields values set forth above are given as % on d.s.)

EXAMPLE 4

Crystallization of Xylitol from Fermented Solution

Xylitol was crystallized from a xylitol-rich solution recovered by chromatographic separation from the fermented solution. The solution which contained 82.5% xylitol of the dry substance was evaporated at 65° C. temperature to 92% concentration. 2200 g of the evaporated solution was seeded with 0.04 mm xylitol seed crystals. The seed amount was 0.03%. The temperature of the solution was lowered to 45° C. in 55 hours according to a predetermined program:

$$T = T_1 - (t : t^1)^2 \times (T_1 - T_2)$$

where
$T$ = the temperature of the solution C
$T_1$ = the temperature at seeding (65° C.)
$T_2$ = the final temperature (45° C.)
$t$ = time from the seeding in hours
$t1$ = total time of crystallization (55 h)

The crystallization was carried out in a vertical crystallizer equipped with a mixer. The crystals were separated from the solution by centrifugation (5 minutes, 2000 g) and washed with water. The recovered crystals had a median size of 0.37 mm and a purity of 99.4% (HPLC).

The foregoing general discussion and experimental examples are intended to be illustrative of the present invention, and are not to be considered as limiting. Other variations within the spirit and scope of this invention are possible, and will present themselves to those skilled in the art.

We claim:

1. A method for the production of xylitol from an aqueous solution which contains xylose and other free hexoses comprising the steps of:
   fermenting said aqueous xylose solution with a yeast strain capable of converting the free xylose present to xylitol, and the free hexoses present in said solution to ethanol, for a period of time sufficient to produce a fermented solution containing xylitol;
   separating xylitol-rich fraction or fractions by chromatographic separation from said fermented solution; and recovering xylitol from said fraction or fractious.

2. The method of claim 1 wherein said yeast genera is Candida or Debaryomyces.

3. The method of claim 2 wherein said yeast strain is *Candida tropicalis.*

4. The method of claim 3 wherein said yeast strain is *Candida tropicalis* having American Type Culture Collection Accession Number 9968.

5. The method of claim 2 wherein said yeast strain is *Debaryomyces hansenii.*

6. The method of claim 1 wherein said xylitol is recovered from said xylitol rich fraction or fractions by crystallization.

7. The method of claim 1 wherein said fermentation is carried out at about 30° C. for about 48 hours.

8. The method of claim 1 wherein said yeast cells are removed by centrifugation after fermentation and before chromatographic separation.

9. The method of claim 1 wherein said yeast cells are removed by filtration after fermentation and before chromatographic separation.

10. The method of claim 1 wherein said chromatographic separation utilizes a cation-exchange resin as column filing material.

11. The method of claim 10 wherein the resin has a divinyl benzene cross-linked sulfonated polystyrene skeleton.

12. The method of claim 1 wherein water is used as eluent in chromatographic separation.

13. The method in accordance with claim 1 wherein said aqueous xylose/hexose solution is a hemicellulose hydrolysate.

14. The method of claim 1 wherein said aqueous xylose/hexose solution is a xylose enriched fraction from sulfide spent liquor.

15. The method in accordance with claim 1 wherein ethanol is removed by evaporation or distillation after fermentation.

16. The method of claim 1 wherein said fermentation is carried out in medium wherein xylose concentration ranges from about 50 g/L to 300 g/L.

17. The method of claim 1 wherein said fermentation is carried out at a pH of between about 3 to about 9.

18. The method of claim 17 wherein said fermentation is carried out at a pH of between about 5 to about 7.

19. The method of claim 1 wherein said fermentation is carried out at a temperature of between about 10° C. to about 45° C.

20. The method of claim 19 wherein said fermentation is carried out at a temperature of between about 25° C. to 35° C.

21. The method of claim 1 wherein said fermentation is carried out with limited oxygen supply.

22. The method of claim 1 wherein components which may be toxic to the yeast used for fermentation or other impurities are separated from said aqueous xylose solution prior to fermentation.

23. The method of claim 22 wherein said separation is carried out by chromatographic separation means.

24. A method for the production of xylitol from solution containing at least 50 g/L xylose and other free hexoses, which comprises the steps of:
fermenting said solution by introducing cells of a yeast strain capable of converting xylose to xylitol, and other hexoses to ethanol for a period of time sufficient to produce xylitol;
separating any xylitol rich fractions by chromatographic separation means; and
recovering at least 90% of the xylitol present in said fractions in crystalline or other forms.

25. The method of claim 24 which said fermentation is carried out at between about 20° C. and about 40° C.

26. The method of claim 25 wherein said fermentation is carried out at about 30° C.

27. The method of claim 24 wherein said fermentation is carried out at a pH of between about 3 to about 9.

28. The method of claim 27 wherein said fermentation is carried out at a pH of between about 5 to about 7.

* * * * *